(12) United States Patent
Bussadori et al.

(10) Patent No.: US 8,391,546 B2
(45) Date of Patent: Mar. 5, 2013

(54) METHOD AND CORRESPONDING APPARATUS FOR QUANTITATIVE MEASUREMENTS ON SEQUENCES OF IMAGES, PARTICULARLY ULTRASONIC IMAGES

(75) Inventors: Claudio Maria Bussadori, Milan (IT); Elena Dall'Aglio, Mediglia (IT); Marco Di Marcello, Brione (IT)

(73) Assignee: Esaote, S.p.A., Milan (IT)

( * ) Notice: Subject to any disclaimer, the term of this patent is extended or adjusted under 35 U.S.C. 154(b) by 1266 days.

(21) Appl. No.: 12/174,182

(22) Filed: Jul. 16, 2008

(65) Prior Publication Data

US 2009/0028404 A1  Jan. 29, 2009

(30) Foreign Application Priority Data

Jul. 23, 2007 (EP) .................... 07112971

(51) Int. Cl.
*G06K 9/00* (2006.01)
(52) U.S. Cl. ......... 382/103; 382/128; 382/131; 382/132
(58) Field of Classification Search .............. 382/128, 382/131, 132; 600/437, 407, 450, 412, 443, 600/447, 409; 345/419
See application file for complete search history.

(56) References Cited

U.S. PATENT DOCUMENTS

| | | | |
|---|---|---|---|
| 2004/0143189 A1* | 7/2004 | Lysyansky et al. ........... | 600/450 |
| 2005/0070798 A1 | 3/2005 | Pedrizzetti et al. | |
| 2005/0228254 A1 | 10/2005 | Torp et al. | |
| 2009/0153548 A1* | 6/2009 | Rabben et al. ............... | 345/419 |

FOREIGN PATENT DOCUMENTS

| | | |
|---|---|---|
| EP | 1520517 A | 4/2005 |
| EP | 1522875 A1 | 4/2005 |
| WO | PCT/EP01/13736 | 6/2002 |

OTHER PUBLICATIONS

Lang, et al. "Recommendations for Chamber Quantification: A Report From the American Society of Echocardiography's Guidelines and Standards Committee and the Chamber Quantification Writing Group, Developed in Conjunction With the European Assoc. of Echocardiography, a Branch of the European Society of Cardiology", Journ. Am. Soc. of Echocardiography, 2005, pp. 1440-1463.

Vannan et al., "Effect of Cardiac Resynchronization Therapy on Longitudinal and Circumferential Left Ventricular Mechanics by Velocity Vector Imaging: Description and Initial Clinical Application of a Novel Method Using High-Frame Rate B-Mode Echocardiographic Images", Echocardiography: A Journ. of CV Ultrasound & Allied Tech., vol. 22, No. 10, 2005, pp. 826-830.

European Search Report for EP 07 11 2971 dated Nov. 15, 2007.

* cited by examiner

*Primary Examiner* — Claire X Wang
(74) *Attorney, Agent, or Firm* — Woodard Emhardt Moriarty McNett & Henry LLP

(57) ABSTRACT

A method for assessing motion, including deformation, of a structure from a sequence of at least two consecutive image frames of such structure, which images are timely separated by a certain time interval. The method including the steps of defining a certain number of reference points at least on one image frame, and determining the velocity of motion of such reference points between two successive image frames.

29 Claims, 17 Drawing Sheets

METHOD AND CORRESPONDING APPARATUS FOR QUANTITATIVE MEASUREMENTS ON SEQUENCES OF IMAGES, PARTICULARLY ULTRASONIC IMAGES

CROSS REFERENCES TO RELATED APPLICATIONS

This application claims the benefit of European Patent Application No. EP07112971, filed Jul. 23, 2007, entitled "METHOD AND CORRESPONDING APPARATUS FOR QUANTITATIVE MEASUREMENTS ON SEQUENCES OF IMAGES, PARTICULARLY ULTRASONIC IMAGES" which is expressly incorporated by reference herein, in its entirety.

BACKGROUND OF THE INVENTION

The invention relates to the technical field of medical imaging, particularly echocardiography imaging.

The assessment of the myocardium (heart muscles) function using echocardiography is a crucial indication in the diagnosis of a patient. The outcome of the myocardium evaluation may significantly influence the patient management and course of treatment.

The main part of the myocardium evaluation is based on the observations of experienced echo-cardiographers, who evaluate myocardial dynamics using B-mode ultrasound imaging during a live scan or using a playback of stored cine-loops. The state of each myocardial segment is estimated according to its temporal dynamics. An experienced echo-cardiographer is often able to visually distinguish between working (viable) myocardial segments and segments with different pathologies.

There are disadvantages to relying on visual distinguishing, however. For example, the estimate may be qualitatively flawed as it is based on an impression from moving images. Also, the examination is significantly affected by intra/inter observer variations of diagnostic quality and reproducibility. Thus, the ultrasound exam may be affected by differing image quality and/or technique. Additionally, significant time is required to achieve the necessary proficiency enabling an echo-cardiographer to reach an accurate diagnosis, and the echo-cardiographer's skills may be negatively impacted if the examination is not performed on a routine basis.

To overcome these drawbacks, several quantitative methods have been proposed for heart muscle assessment. A strain rate analysis method in ultrasonic diagnostic imaging is disclosed in WO 02/45587. According to this document strain rate analysis is performed for ultrasonic images in which the spatial gradient of velocity is calculated in the direction of tissue motion. Strain rate is calculated for cardiac ultrasound images in the direction of motion which, for myocardial images, may be either in the plane of the myocardium or across the myocardium. Strain rate information is calculated for a sequence of images of a heart cycle and displayed for an automatically drawn border such as the endocardial border over the full heart cycle. The spatial gradient of velocity used for determining the strain and the displacements of the borders form one frame to a successive one in a sequence of frames uses so called Doppler Tissue Imaging, so called DTI. This technique allows to measure tissue velocity over all points in the ventricular wall. The measurement of velocity itself provides a direct information about the wall motion and helps to uncover abnormalities not immediately observable from the visualization in B-mode. The velocity contains information about either rigid body displacement, shear, and contraction/distension, the latter being immediately related to the myocardial activity. Post processing of the DTI velocity data allows the evaluation of additional quantities, namely strain-rate and strain, that are strictly related to the regional function. Segmental strain gives a direct evaluation of the degree of contractility of the myocardium during systole, as well as of its relaxation during ventricular filling.

Doppler tissue imaging suffers of an intrinsic limitation due to the fact that only the component of velocity along a scanline can be measured. When tissue moves in a direction that is not aligned with the scanline, the Doppler velocity does not reflect the effective tissue kinematics. Only the component of strain and strain rate along the scanline can be evaluated correctly, giving a reduced view of the local deformation state. This limits the application of DTI to the anatomic sites that can be imagined aligned along a scanline. In echocardiography this corresponds essentially to the interventricular septum and to the lateral walls in apical view.

Improved quantitative methods for assessing motion and deformation of tissue or objects, which do not suffer from this limitation, are based on border tracking algorithms which allow to estimate velocity at a set of points on a contour of a moving tissue or object without the need to refer to Doppler analysis. By tracking the border on each image frame of a sequence of image frames, it is in fact possible to determine the instant velocity of a certain number of selected points on the border as a function of the difference in position of such points in consecutive image frames in the time interval, as taught, for example, in EP-A-1522875 or US2004/0143189. The velocity so determined can thus be displayed, for example, as a vector overlaid onto the B-mode image where the length of the vector indicates the magnitude of the tissue or object velocity, and the direction of the vector indicates the direction in which the tissue or object is moving as shown, for example, in FIGS. 1 and 2. Alternatively or in combination, the magnitude of the tissue velocity of each, or selected reference points, and thus strain/strain rate can be displayed as a diagram in function of time.

As disclosed and as used herein, the reference to "tissue or objects" is intended to be inclusive, and "structure" is used to include both. Further, since deformation would inherently involved some "motion", use of the term, motion, is intended to include deformation.

Such methods, although potentially enabling the clinician to evaluate quantitatively myocardial dynamics using B-mode ultrasound imaging during a live scan or using a playback of stored cine-loops, are still too operator-dependent. As the clinician chooses the reference points on the basis of his experience, the resulting numerical data show a high variability which prevents these methods from being exploited in full. Although the indication in real time of the velocity vectors and/or strain of some reference points on a tracked endocardial border has been found useful in Cardiac Resynchronization Therapy (CRT) as disclosed, for example, in Vannan et al.: "Effect of Cardiac Resynchronisation Therapy on Longitudinal and Circumferential Left Ventricular Mechanics by Velocity Vector Imaging: Description and Initial Clinical Application of a Novel Method Using High-Frame-Rate B-Mode Echocardiographic Images", Echocardiography, vol. 22, n. 10, November 2005, pages 826-830, these methods are presently used only as qualitative visual aids which play a minimal role in a full quantitative assessment of the dynamics of the hearth.

Furthermore, the not optimised choice of the points of the border to be tracked also affects the functioning of the algorithm performing the tracking itself and hence the accuracy of the quantitative measurements. In fact, it may happen that if a reference point is placed too close to the valve leaflet, the movement of such leaflet is tracked instead of the endocardial border with an erroneous estimation of velocities and/or strain values.

All these problems have been partially solved improving the skill of the operator, however the intrinsic problem related to reproducibility of measures still exists due to both inter and intra-operator dependency. Not reproducibility means high variability of results which do not allow one to determine values to be used as indicators of a state of illness. This can be extended also to non-medical fields, like not-destructive testing, where such indicators could be, for example, critical rupture points/lines in a deformed structure.

An object of the present invention is to solve, at least partially, one or more of the above-mentioned problems by providing a method capable of obtaining reproducible quantitative measures from a sequence of images.

The invention achieves the aim with a method for assessing motion and/or deformation of a moving tissue or object from a sequence of at least two consecutive image frames of such tissue or object, which images are timely separated by a certain time interval, the method comprising the following steps:
defining a certain number of reference points at least on one image frame of the sequence of image frames;
determining the velocity of motion of such reference points between two successive image frames;
wherein
the at least one image frame is rescaled to fit within a reference window;
a reference image is superimposed on such rescaled image frame;
the reference points are defined by matching points on the rescaled image frame to corresponding points on the reference image.

Alternatively or in combination the reference image can be rescaled to fit with the dimensions of the image frame and/or the reference window.

By appropriately choosing the reference image is possible to consistently determine the reference points which are representative of motion and/or deformation of the tissue or object under examination, thus reducing inter and intra-operator variability as the superimposed reference image acts as a guide for determining such reference points. Particularly the reference image comprises line or curve segments, which are preferably part of concentric lines regularly angularly spaced, and the reference points are defined by the intersection of such segments with a border line of the tissue or object automatically or manually drawn on the image frame. The reference image is advantageously aligned on the image frame with the help of landmarks, i.e. representative points or segments identified on the image frame, like, for example, easily discernible anatomic features.

The sequence of image frames is typically a sequence of consecutive B-mode, grey scale ultrasound images. The reference points are taken on a border line identified on at least one image of the sequence either manually or by means of an automatic border detection algorithm. Such border is tracked to determine the new position of the reference points in at least one following image frame of the sequence so as to estimate the instant velocity of each reference point on the border line by dividing the displacement vector of each of the reference points from consecutive image frames by the time interval occurred between said consecutive image frames. In case of echographic images of the hearth, the border can be, for example, the endocardial border.

According to an embodiment, the sequence of images frames represents the long axis view of the left ventricle. In this case the landmarks which can be used to align the reference image are points identifying the cardiac apex and each of the two extremities of the annulus. The reference image is formed by a vertical line intersected by a number of divergent segments, preferably concentric, symmetrically disposed with reference to a median orthogonal segment. The superimposition of the reference image on the at least one image frame comprises the steps of rototraslating the reference image to bring the upper segment to intercept the apex point, the lower segment to intercept one of the two annulus points and the median segment to be substantially orthogonal to the line passing through the apex and said one of the two annulus points. The segments forming the reference image are typically 7, some or all the reference points on the at least one image frame being defined by the intersection of such segments with the endocardial border lying between the apex and said one of the two annulus points. By repeating these steps for both the points of the annulus, it is thus possible to take the reference points on all the endocardial border. They are typically 13, three of them being the reference points respectively taken on the apex and on both the extremities of the annulus, the remaining 10 points being defined by alternatively choosing one of the two annulus points to determine 5 reference points on the septum endocardiac border and 5 reference points on the free wall endocardiac border.

According to an embodiment, the sequence of images frames represents the short axis basal or mid-cavity view. In this case the landmark is a segment passing through the mitral valve or the papillar muscles. The reference image is formed by a bundle of concentric regularly angularly spaced lines, two lines of the bundle being orthogonal. The superimposition of the reference image on the at least one image frame comprises the steps of rototraslating the reference image to bring one of the two orthogonal lines parallel to the landmark segment and the centre of the bundle in the middle of the ventricular cavity. The orthogonal lines are advantageously provided with scales to guide the positioning of the centre of the bundle in the middle of the ventricular cavity. The lines are typically 6, the reference points on the at least one image frame being defined by the 12 intersections of such lines with the endocardial border.

According to another embodiment, the sequence of images frames represents the short axis apex view. The reference image is now formed by a bundle of concentric regularly angularly spaced lines, two lines of the bundle being orthogonal. The reference image is superimposed on the at least one image frame with the centre of the bundle in the middle of the ventricular cavity. As no further anatomical landmarks can be determined in this view, the angular displacement of the reference image is determined by positioning one of the two orthogonal lines parallel to a landmark segment previously determined and stored while performing the steps provided for determining the reference points for the corresponding short axis basal or mid-cavity view as seen above. The lines are typically 4, the reference points on the at least one image frame being defined by the 8 intersections of such lines with the endocardial border.

Advantageously the reference points on each image frame identify segments into which the left ventricle can be divided, for example according to the recommendation of the American Society of Echocardiography as disclosed e.g. in Lang et al. "Recommendations for Chamber Quantification: A Report from the American Society of Echocardiography's Guidelines and Standards Committee and the Chamber Quantification Writing Group, Developed in Conjunction with the European Association of Echocardiography, a Branch of the European Society of Cardiology", Journal of the American Society of Echocardiography, vol. 18, Number 12, 2005, pp. 1440-1463. Each segment is identified by a series of three consecutive reference points, the median point of the series being taken as the representative point for assessing motion and/or deformation of each segment. Advantageously motion and/or deformation is assessed by determining the velocity of motion and/or strain rate of such median reference points between consecutive image frames. This way of choosing the reference points is very powerful as it allows to have a direct and immediate understanding of the dynamics of each regional segment and thus of the hearth.

According to another aspect, the invention relates to an apparatus for assessing motion and/or deformation of a moving tissue or object from a sequence of at least two consecutive image frames of such tissue or object, which images are timely separated by a certain time interval. The apparatus comprises input means for receiving the position of representative landmarks on at least one image of the sequence, for example by an operator, and processing means programmed for determining reference points representative of motion and/or deformation of the tissue or object by scaling and/or superimposing said at least one image with a reference image. The landmarks are used for aligning said reference image onto said at least one image of the sequence. The reference points are determined by the intersection of a border line of the tissue or object with line or curve segments forming said reference image.

According to an embodiment, motion and/or deformation of the tissue or object is evaluated by determining the velocity of motion of such reference points between two successive image frames by using Doppler methods and/or by tracking the movement of such reference points in consecutive image frames and dividing the displacement vector of each of the reference points from consecutive image frames by the time interval occurred between said consecutive image frames, as disclosed for example in EP-A-1522875 or by applying the so called particle image velocimetry technique abbreviated as PIV, as disclosed for example in EP-A-1520517.

Advantageously, deformation of the tissue or object is evaluated by determining the spatial derivatives of velocities of the reference points which can be further integrated to obtain an estimation of strain.

According to another aspect, the invention relates to an image ruler, like for example a transparency film, comprising a series of diverging lines adapted to be manually positioned on a screen displaying at least an image frame of a sequence of image frames of a tissue or object to determine reference points representative of motion and/or deformation of such tissue or object by performing one or more of the method steps according to the invention.

Further improvements of the invention will form the subject of the dependent claims.

The characteristics of the invention and the advantages derived therefrom will be more apparent from the following description of non-limiting embodiments, and as illustrated in the drawings.

BRIEF SUMMARY

A method for assessing motion, including deformation, of a structure from a sequence of at least two consecutive image frames of such structure, which images are timely separated by a certain time interval. The method including the steps of defining a certain number of reference points at least on one image frame, and determining the velocity of motion of such reference points between two successive image frames.

One object of the present disclosure is to provide an improved method for quantitative measurements on sequences of ultrasonic images.

DETAILED DESCRIPTION

Figure 1:
FIG. 1 shows an echographic image of the left ventricle, in long axis view (from the apex to the mitral plane), extracted from an echocardiographic recording with an endocardial border (white) and the instant border velocity (white).

For the purposes of promoting an understanding of the disclosure, reference will now be made to the embodiments illustrated in the drawings and specific language will be used to describe the same. It will nevertheless be understood that no limitation of the scope of the disclosure is thereby intended, such alterations and further modifications in the illustrated device and its use, and such further applications of the principles of the disclosure as illustrated therein being contemplated as would normally occur to one skilled in the art to which the disclosure relates.

The present disclosure makes reference to two-dimensional sequences (loop) of B-Mode ultrasonic images of the heart. The invention is, however, not to be considered limited to this specific application as it can be used for assessing motion and/or deformation of any type of moving object for which sequences of two-dimensional or three-dimensional images are available. They could be series of pictures or RX or ultrasound images of a structure under mechanical stress, for example, in the field of not destructive testing, or images resulting from angiography, TC, SPECT, PET or MRI investigations. In this case heart is the preferred target, however also other type of moving organs can be the object of the investigations.

The method according to the present disclosure allows to assess motion and/or deformation of an object, particularly the heart, by determining the velocity of properly selected reference points on a line drawn to represent an imaged wall or border of such object. Such velocities can be measured using known Doppler techniques, such as DTI, or by tracking the border and thus measuring displacements of such reference points in consecutive images as taught, for example, by EP-A-1522875. According to this document, the myocardial border is tracked over the time starting from one reliable existing instantaneous trace or border line, either drawn by the physician over one single frame or determined by automatic border detection algorithm. After that, an analysis is performed on a pixel-by-pixel brightness basis allowing the compensation of movements of cardiac segments (translation, lengthening, thickening) and the evaluation of the punctual velocity.

The velocity is typically displayed as a vector overlaid onto the B-mode image where the length of the vector indicates the magnitude of the tissue velocity representation.

Figure 2:
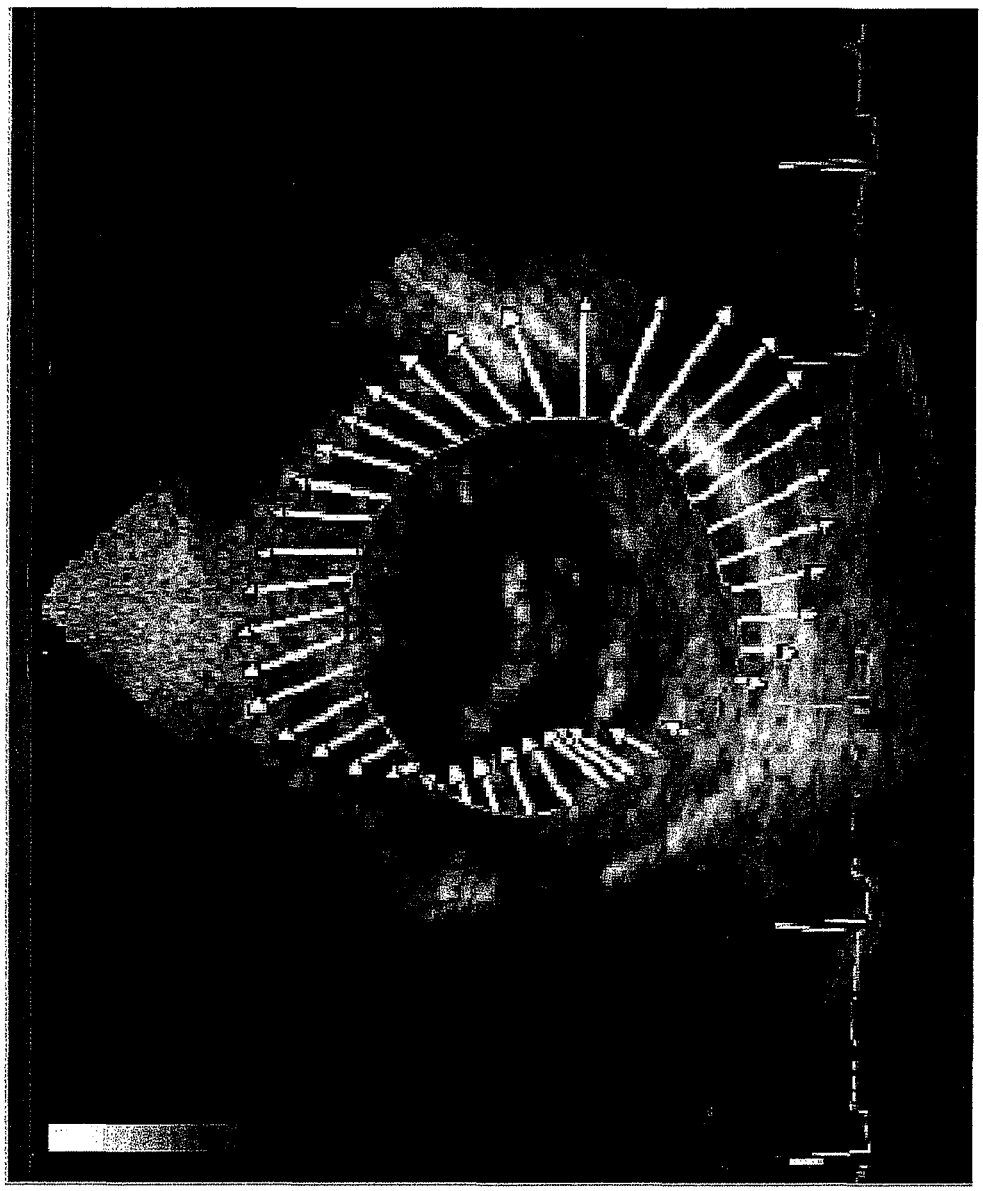
FIG. 2 illustrates an echographic image of the left ventricle, in short axis view (transversal section), extracted from an echocardiographic recording with an endocardial border (white) and the instant border velocity (white).
Figure 3:
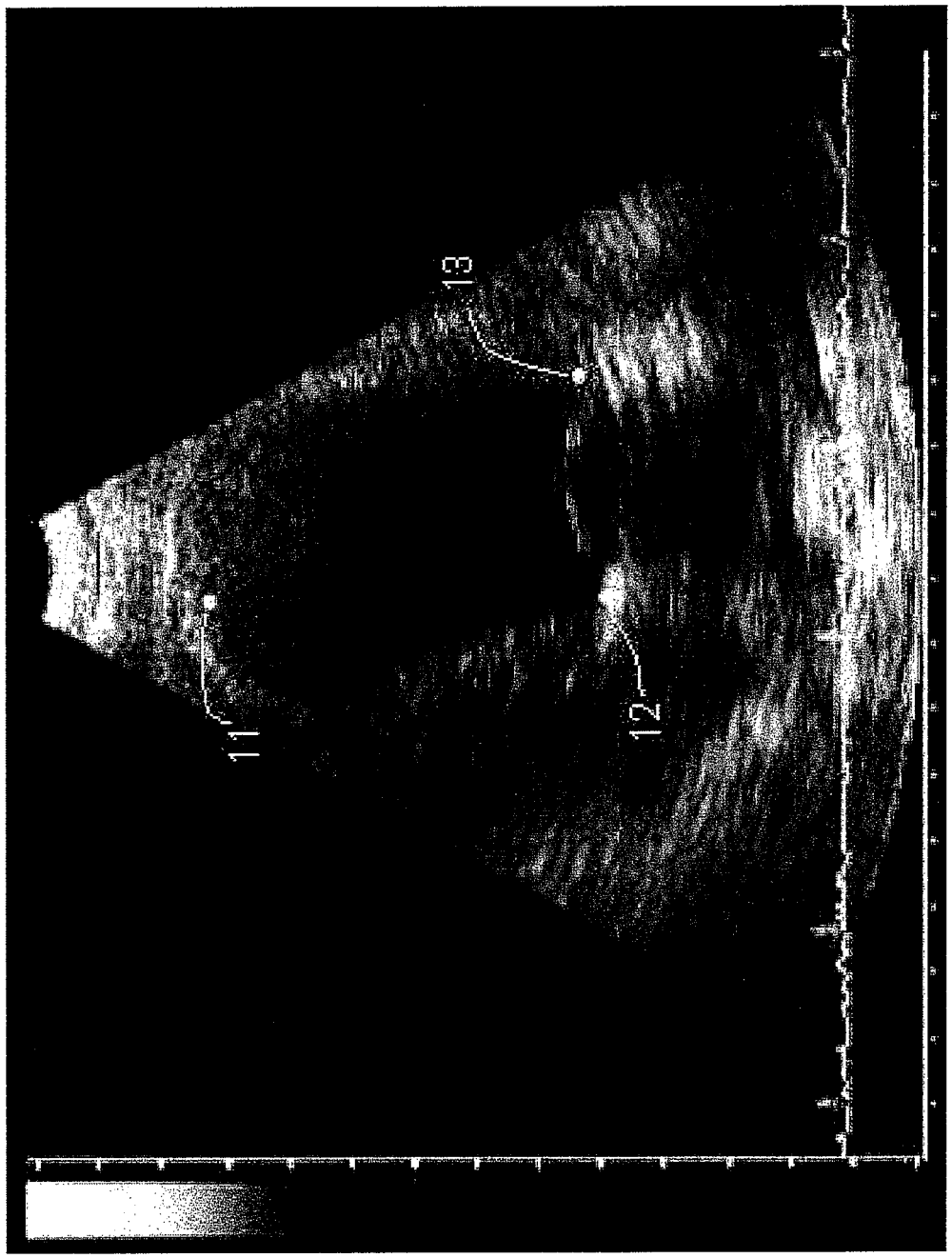
FIG. 3 shows a long axis view of the left ventricle with reference points identifying the apex and both the extremities of the annulus.

FIGS. 1 and 2 illustrate an example of such results respectively in a long axis view and in a short axis view of the left ventricle where the border line and the instant velocity vectors at certain reference points on the said borderline are shown superimposed on the B-mode image.

When a sequence of image frames is acquired, the border line and/or at least the reference points on it are tracked over every frame of the sequence and the velocity vector at each reference point is determined and displayed as a function of the difference in position of the reference point in a preceding and in a following frame and of the time interval between the these frames. Thus the velocity vectors on the screen may vary with time if a sort of cinema view is carried out.

As already explained, the instant velocities, determined by using Doppler or border tracking techniques or any other means, contain information about the dynamical behaviour of the object, in this case the left ventricle wall. In order to be able to use this information for correlating mechanical behaviour to physiological meaning so that only relevant information is furnished to the specialized person, the invention provides for a method allowing to choose the reference points upon which reproducible quantitative measures from a sequence of images can be obtained. Such quantitative measures may be the instant velocities, but also global quantities (like volumes, lengths) as well as local phenomena (like rotations, strain, strain rate).

Figure 13A:
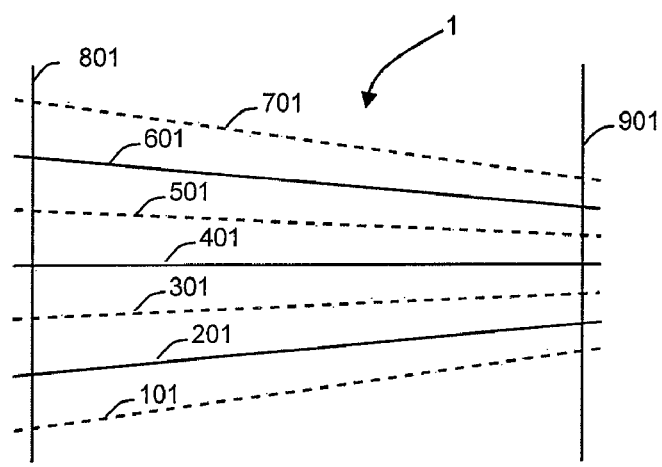
FIG. 13 shows three exemplary image rulers according to the invention to be used respectively for long-axis views (FIG. 13a), papillary muscle (SAX PM) or mitral valve (SAX MV) short-axis views (FIG. 13b) and apex short-axis views (FIG. 13c).

FIG. 3 to 8 show how thirteen reference points can be consistently taken on an echographic image of the left ventricle in long axis view. In this projection, three anatomic landmarks are clearly identifiable: the apex 11 and the extremities of the annulus 12, 13 (see FIG. 3). These points are used as a guide for positioning the image ruler 1 of FIG. 13a on the image for determining all the reference points of the endocardial border which will be used for assessing motion and/or deformation. This ruler 1 has seven equally-angularly spaced segments (101 to 701) belonging to corresponding concentric lines and delimited by two vertical segments 801, 901 orthogonal to the middle segment 401.

Figure 4:
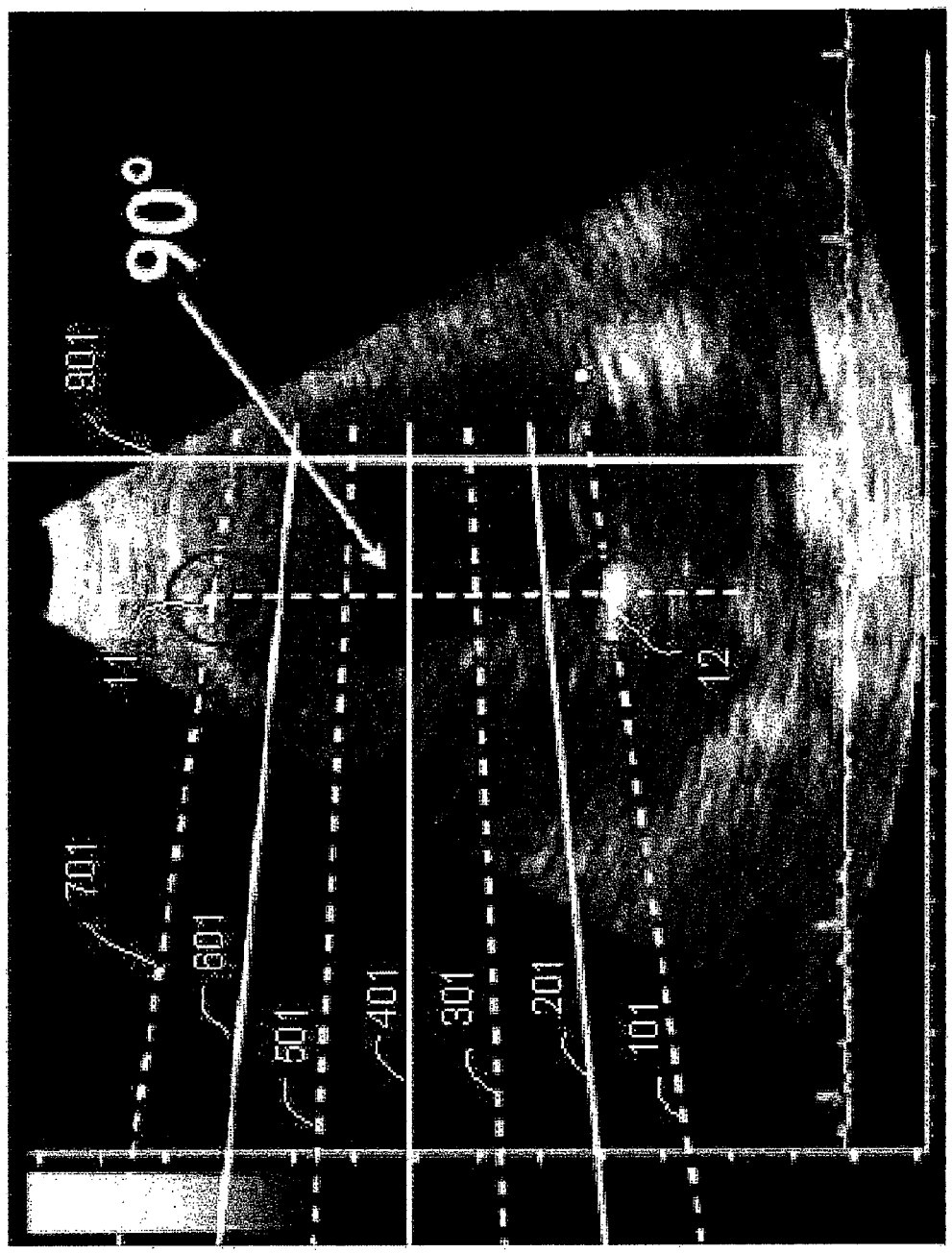
FIG. 4 shows the image of FIG. 3 with an image ruler superimposed to obtain reference points on the septum as depicted in FIG. 5.
Figure 5:
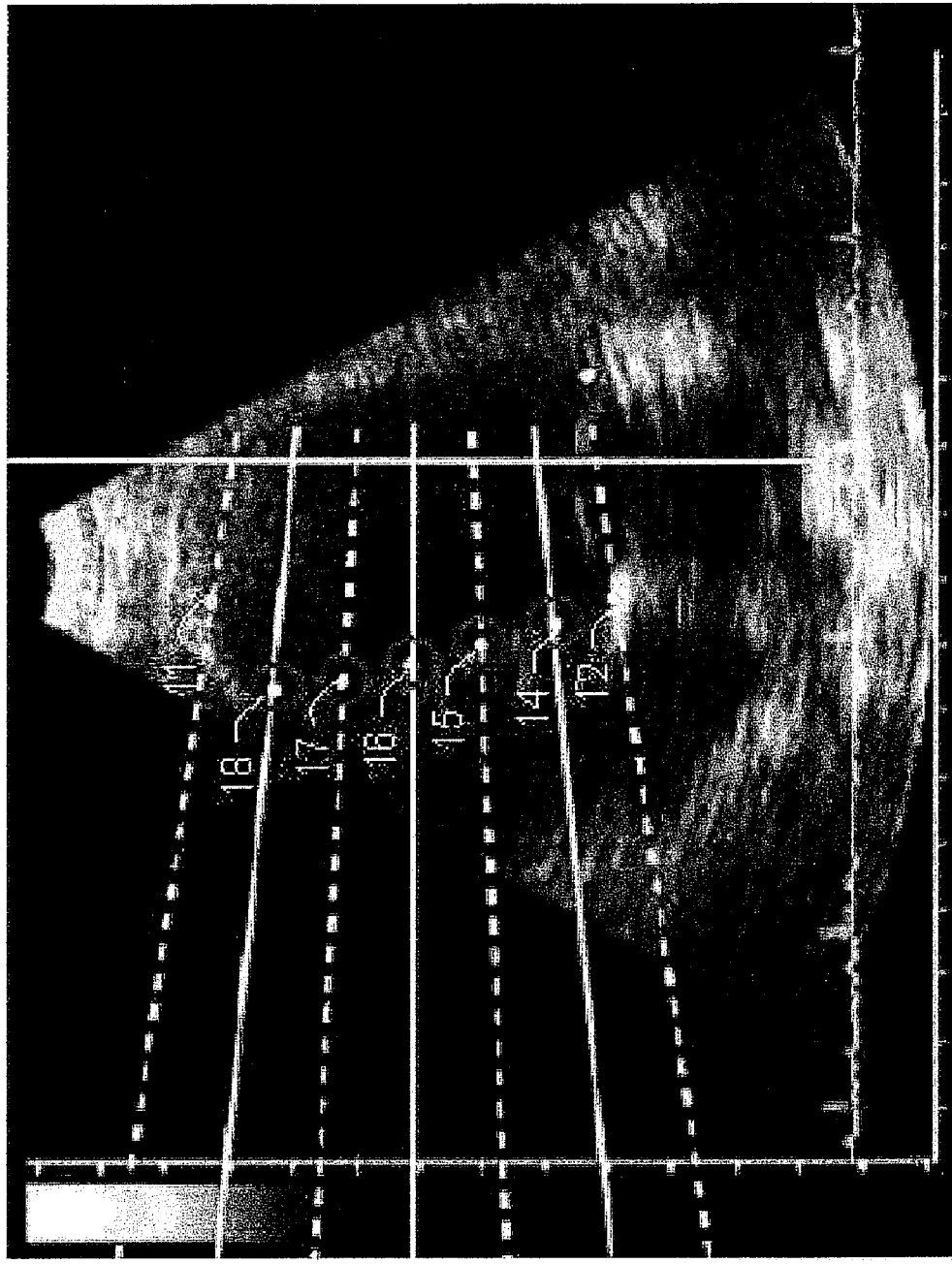
FIG. 5 shows the image of FIG. 3 with the reference points shown.
Figure 6:
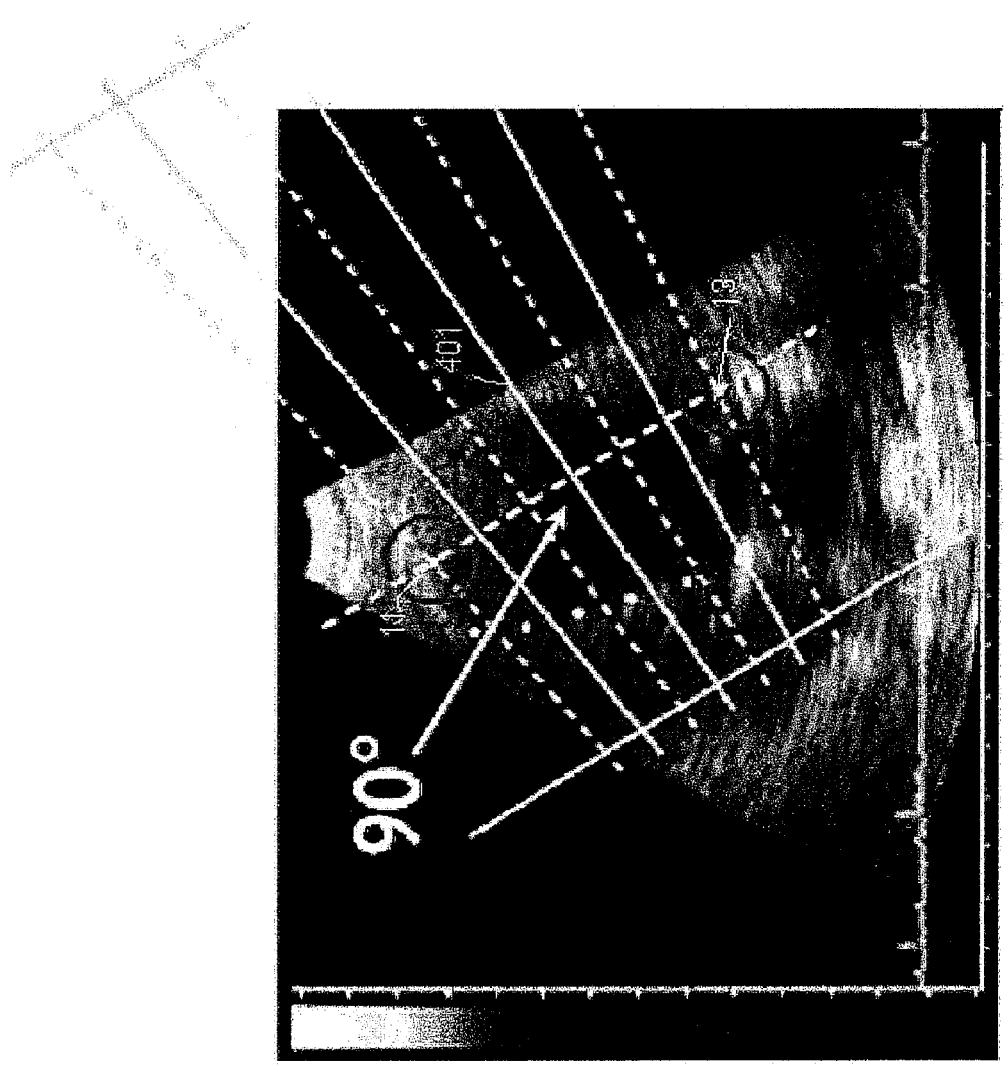
FIG. 6 shows how the image ruler of FIG. 4 can superimposed to determine the reference points on the lateral wall as depicted on FIG. 7.

With reference to FIG. 4, the image ruler 1 is positioned on the echographic image so that the external segments 701 and 101 respectively intercept the apex point 11 and the left annulus point 12 (the one close to the septum) with the middle segment 401 orthogonal to the line passing through such points 11 and 12. Before such operation the echographic image can be resealed to properly fit a window which size is optimised for the dimensions of the reference image. Alternatively or in combination the reference image is resealed to properly fit with the dimensions of the echographic image. The reference points on the septum are thus determined by the intersection between the five segments 201 to 601 with the septum endocardial border as shown by the circles 14 to 18 in FIG. 5. To determine the remaining reference points a similar procedure is followed: ruler 1 is rotated so as the segments diverge towards the free endocardial wall and positioned so that that the external segments 701 and 101 respectively intercept the apex point 11 and the right annulus point 13 (the one close to the endocardial free wall) with the middle segment 401 orthogonal to the line 112 passing through such points 11 and 13. The reference points on the free wall are thus determined by the intersection between the five segments (201 to 601) with the free-wall endocardial border as shown by the circles (19 to 23) in FIG. 7. The whole resulting reference points (11 to 23) located on the endocardial border are shown in FIG. 8.

FIG. 9 to 12 show how twelve reference points can be consistently taken on an echographic image of the left ventricle in short axis view at the level of the papillary muscles. In this projection, a line passing through the papillary muscles represent the anatomic landmark to be used for positioning the ruler 2 of FIG. 13b on the image for determining all the reference points of the endocardial border. The ruler 2 consists of a bundle of six equally-spaced concentric segments (102 to 602) each divided in two halves by the centre 702 of the bundle and having graduated median orthogonal segments 102, 402.

Figure 9:
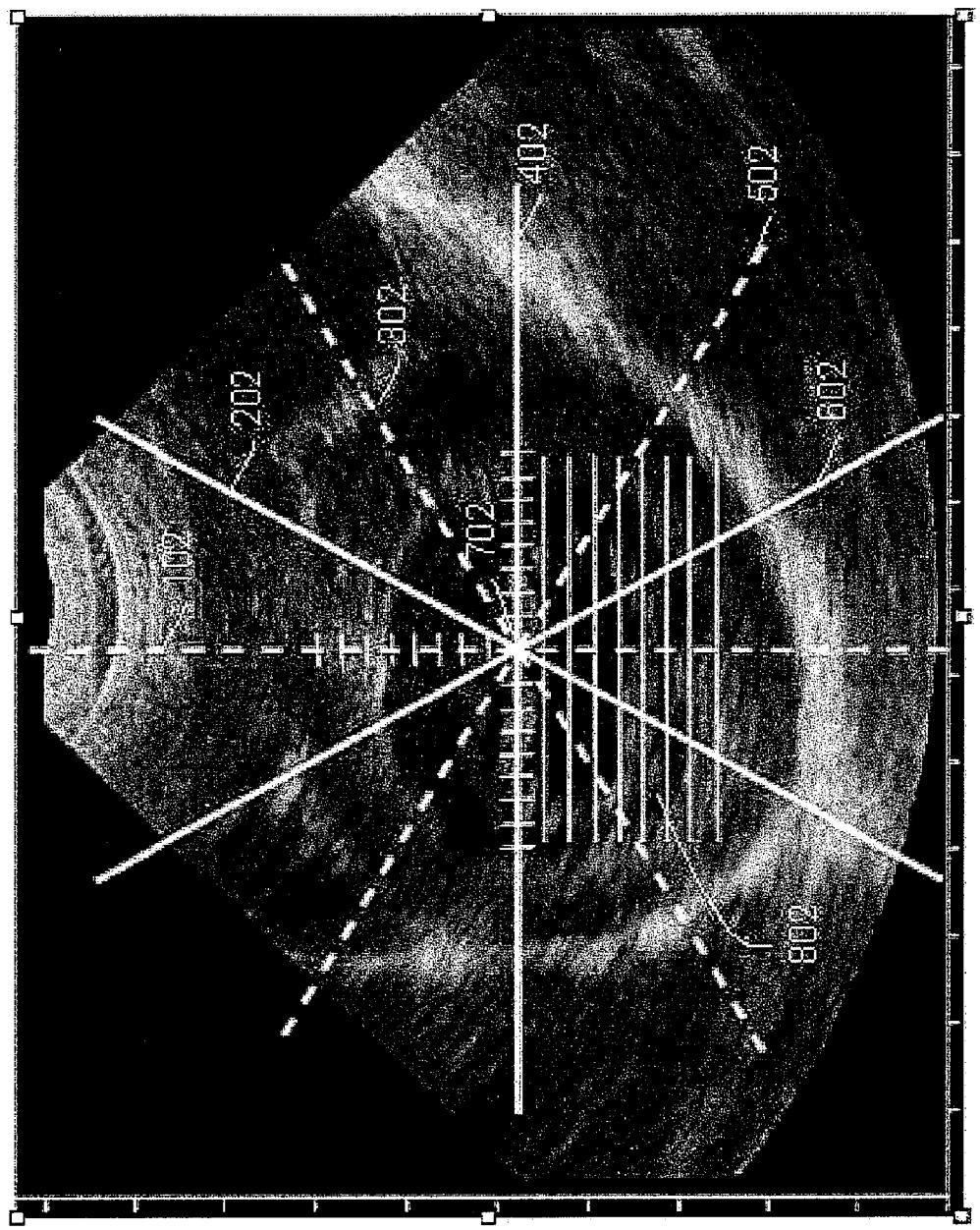
FIG. 9 shows a SAX PM, i.e. a short axis view of the left ventricle at the level of the papillary muscle with a superimposed image ruler.
Figure 10:
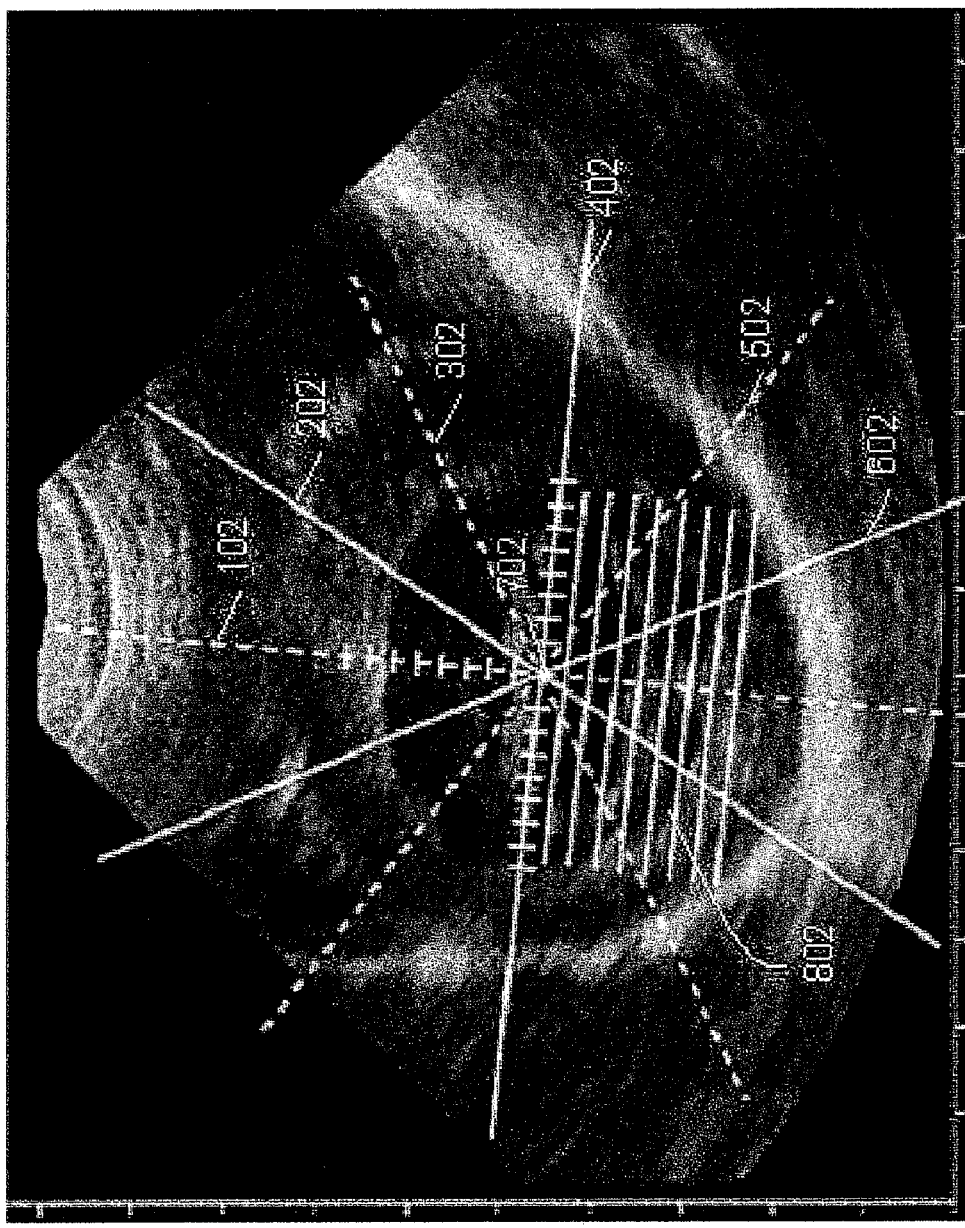
FIG. 10 shows the image of FIG. 9 with the ruler positioned with centre in the middle of the ventricular cavity and horizontal axis parallel to the mitral valve leaflet.
Figure 11:
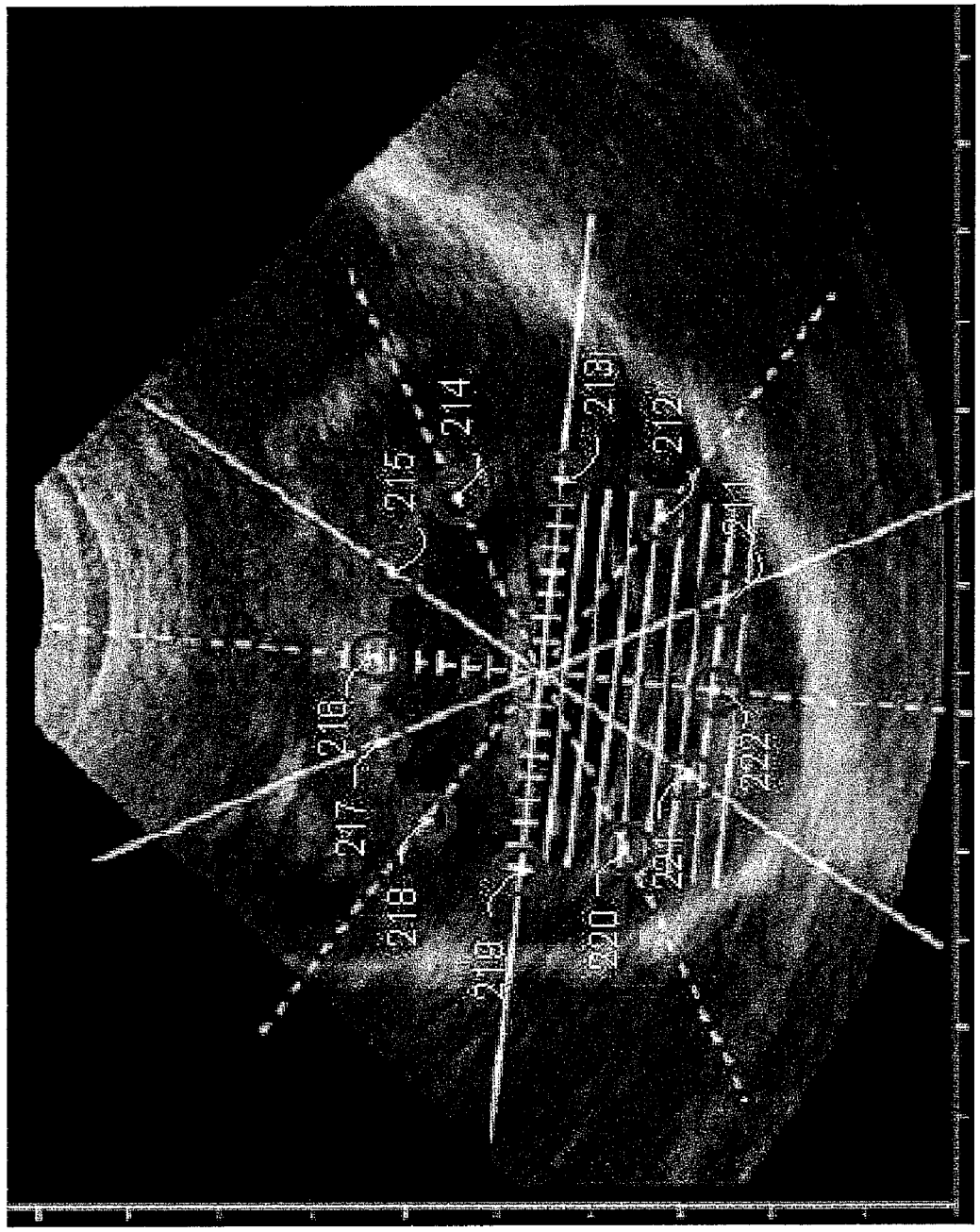
FIG. 11 shows the intersections between the segments of the ruler with the endocardial border.
Figure 12:
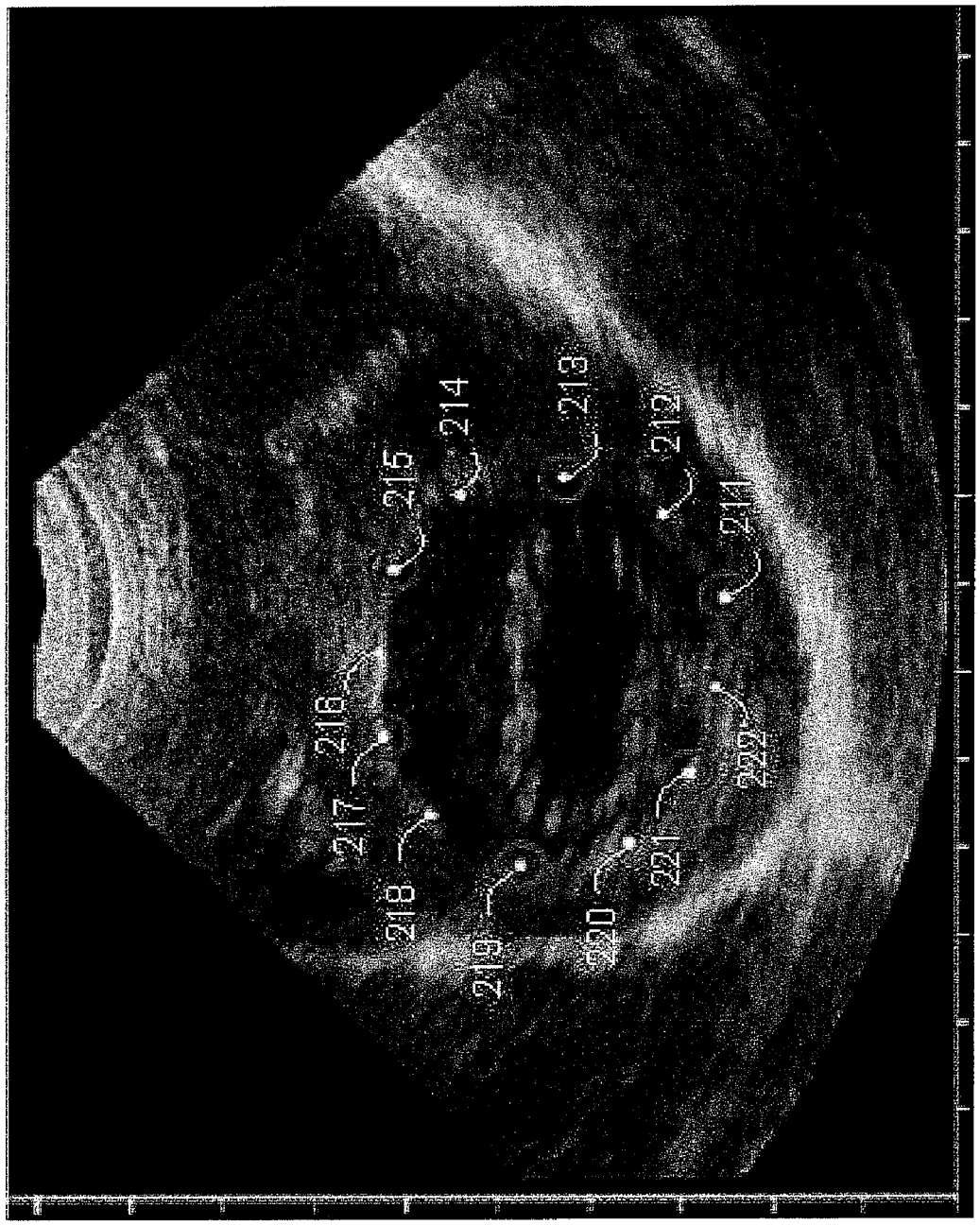
FIG. 12 shows the resulting twelve reference points on the image of FIG. 9.

With reference to FIGS. 9 and 10, the image ruler 2 is first positioned on the echographic image and thus rototraslated to superimpose the horizontal median segment 402 on the valve leaflet with the centre 702 in the middle of the ventricular cavity. The centre of the cavity is determined with the help of scale and auxiliary segments 802 parallel to the median horizontal segment 402. The reference points are thus determined by the intersection between the segments with the endocardial border as shown by the circles in FIG. 11. The whole resulting reference points located on the endocardial border are shown in FIG. 12.

Figure 7:
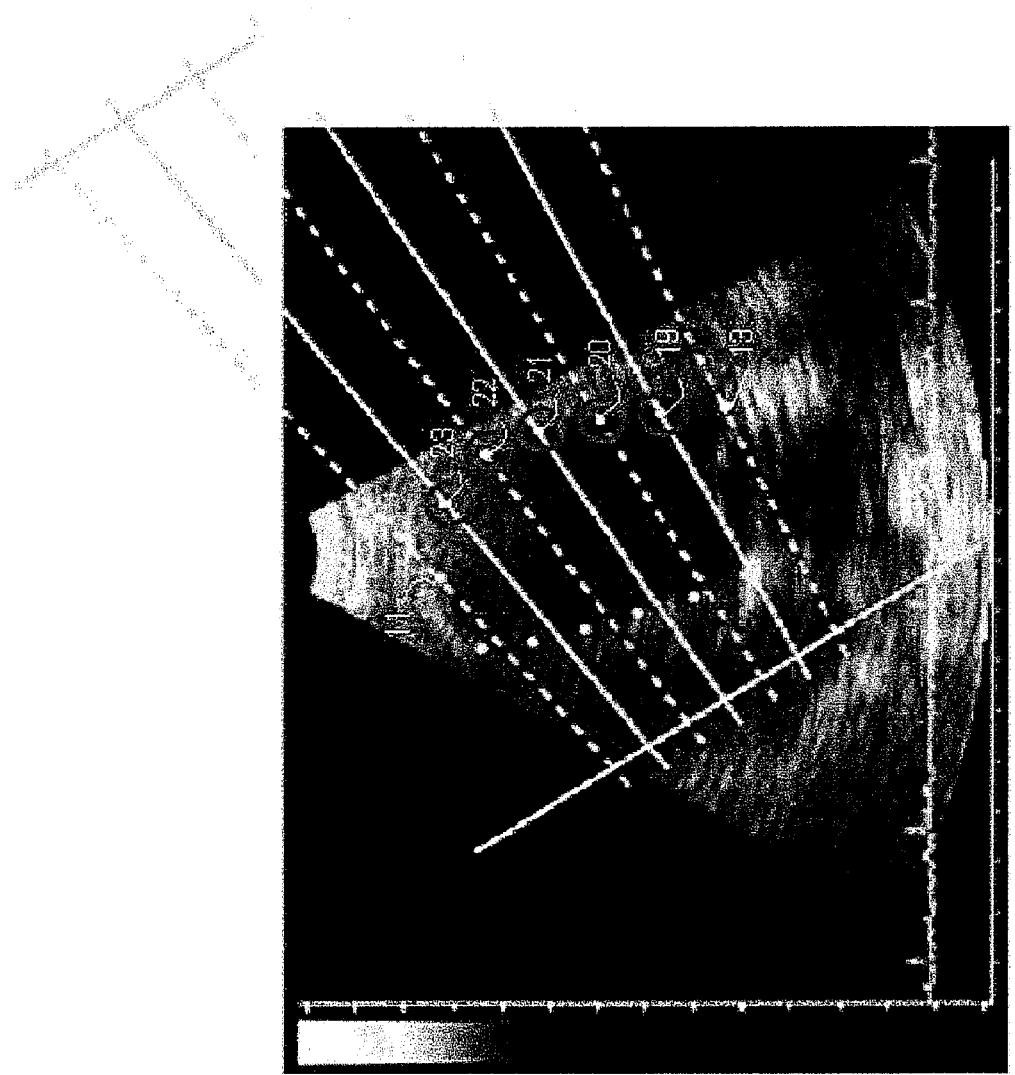
FIG. 7 shows the image of FIG. 3 with the reference points on the lateral wall.
Figure 8:
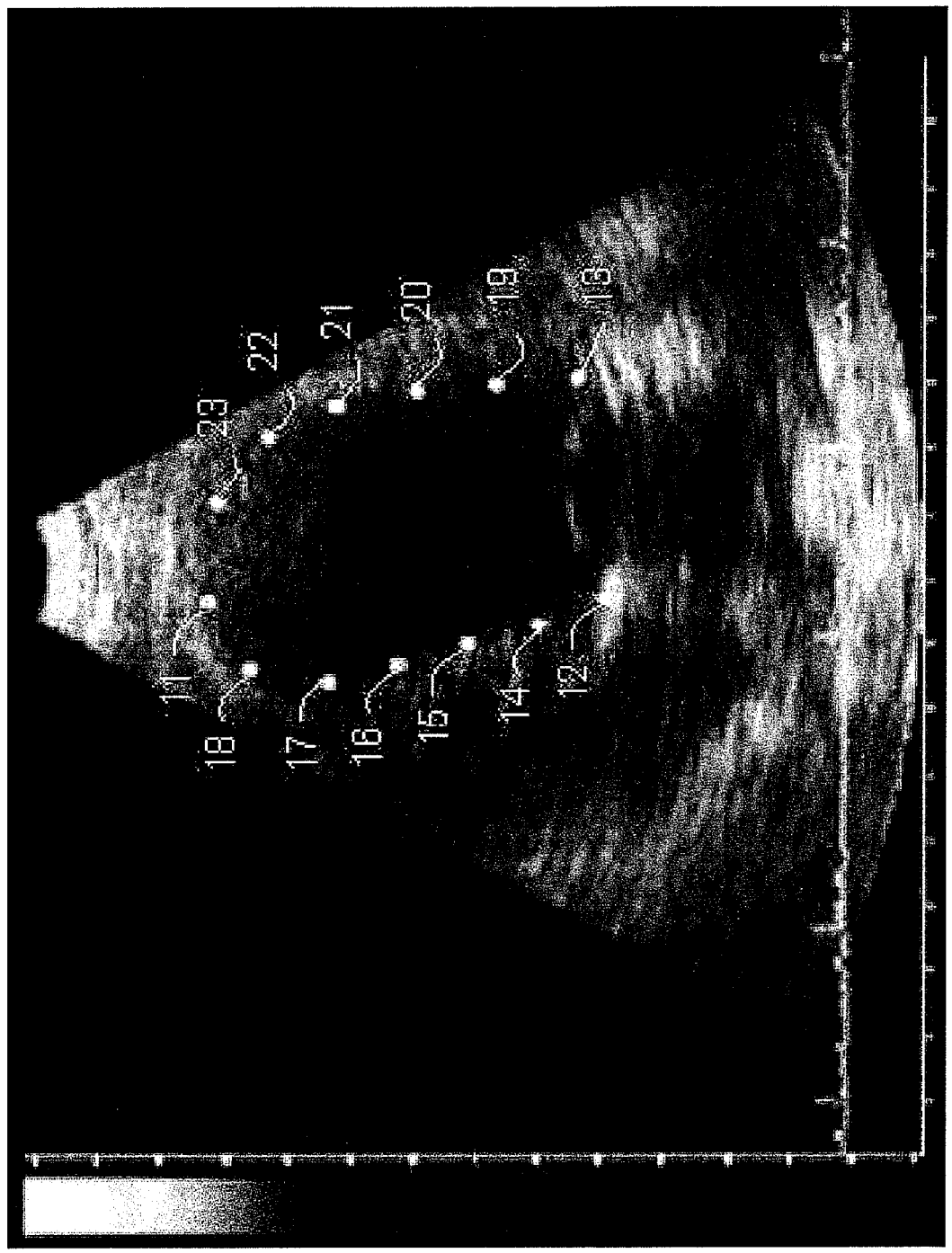
FIG. 8 shows the resulting thirteen reference points taken on the whole endocardial border in the long axis view of the left ventricle of FIG. 3.
Figures 13B, 13C:
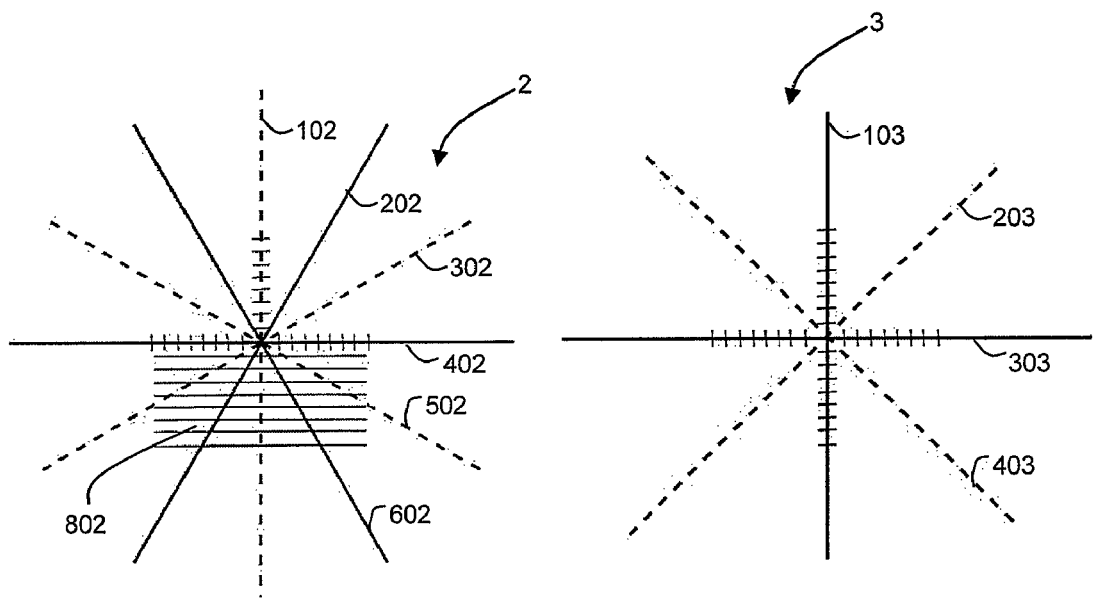

By using the ruler 3 of FIG. 13c, 7 reference points can be taken on an echographic image of the left ventricle in short axis view at the level of the apex. The ruler 3 is similar to ruler 2, but with four segments 103, 203, 303, 403 instead of six in order to determine eight reference points on the endocardial border. In this view no anatomical landmarks are present hence the ruler has to be positioned on the image without guide. Only the centre of the cavity can be determined with the help of the scale and auxiliary parallel segments as seen above. The orientation of the horizontal segment 303 can be found by aligning it with the position of the papillary leaflet previously determined in a short axis view at the level of the papillary muscles or the mitral valve as seen before and advantageously stored in a memory means.

Figure 14B:
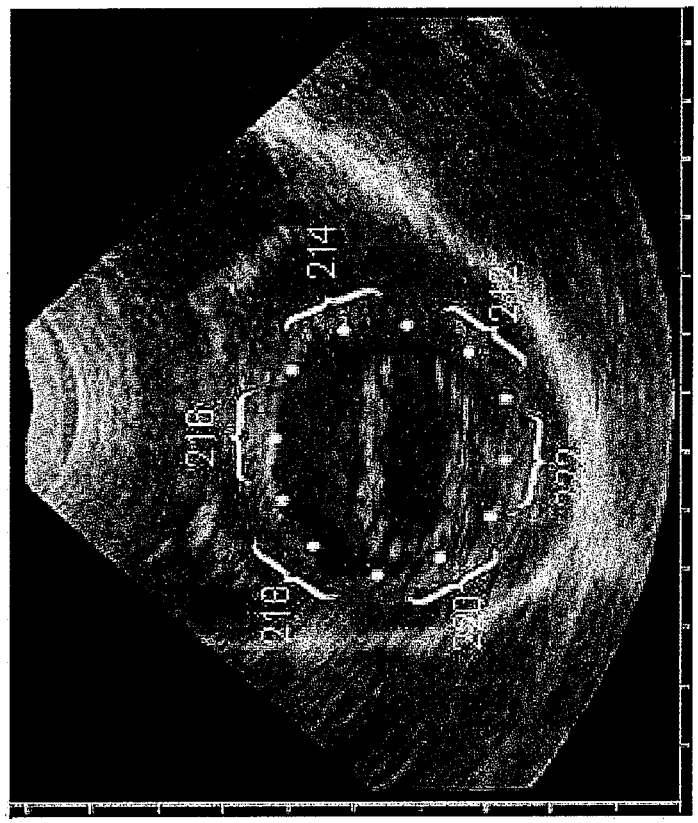
FIG. 14 shows how the reference points (FIGS. 14a and 14b) can be used to identify regional segments on the left ventricle, namely six segments in a long axis view (FIG. 14c) and six segments in papillary muscle or mitral valve short-axis view (FIG. 14d).

The number of reference points to be used in each view can be advantageously determined to obtain a meaningful segmentation of the heart such as the one proposed by the American Standard of Echocardiography. With reference to FIG. 14, each segment can be identified by a series of three consecutive reference points, the median point of the series (14, 16, 18, 23, 21, 19; 212, 214, 216, 218, 220) being taken as the representative point for assessing motion and/or deformation of each segment. Advantageously motion and/or deformation is assessed by determining the velocity of motion and/or strain and/or strain rate of such median reference points between consecutive image frames. This way of choosing the reference points is very powerful as it allows to have a direct and immediate understanding of the dynamics of each regional segment and thus of the hearth. In the example of FIG. 14 the endocardial border is divided into six regional segments both in the long axis view (FIGS. 14*a* and 14*c*) and in the short axis view (FIGS. 14*b* and 14*d*).

Figure 14A:
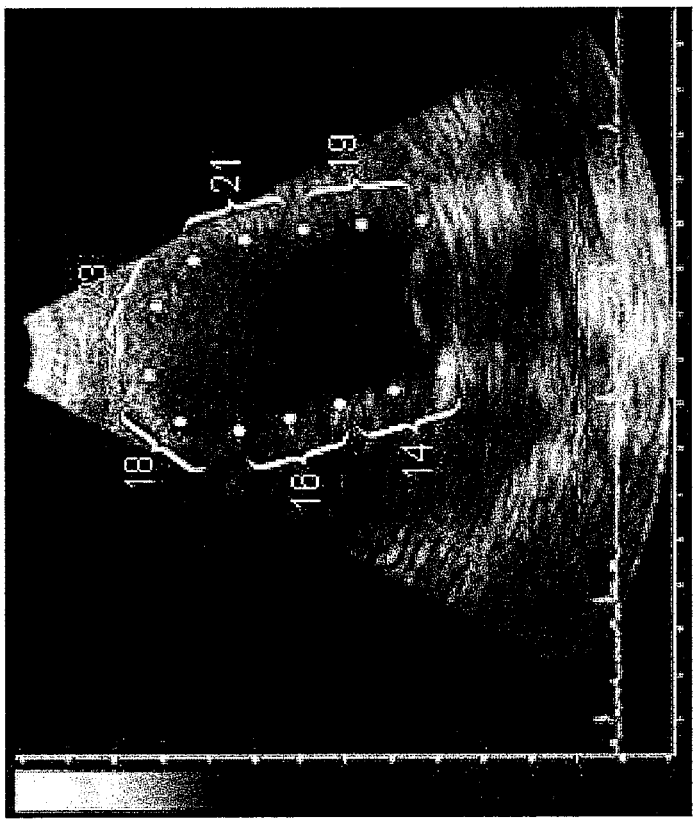
Figure 14D:
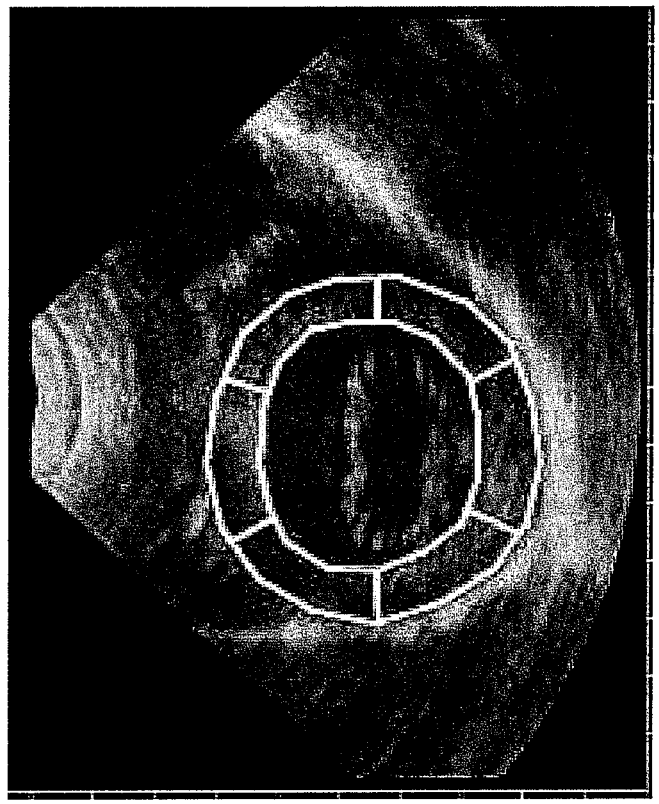
Figure 14C:
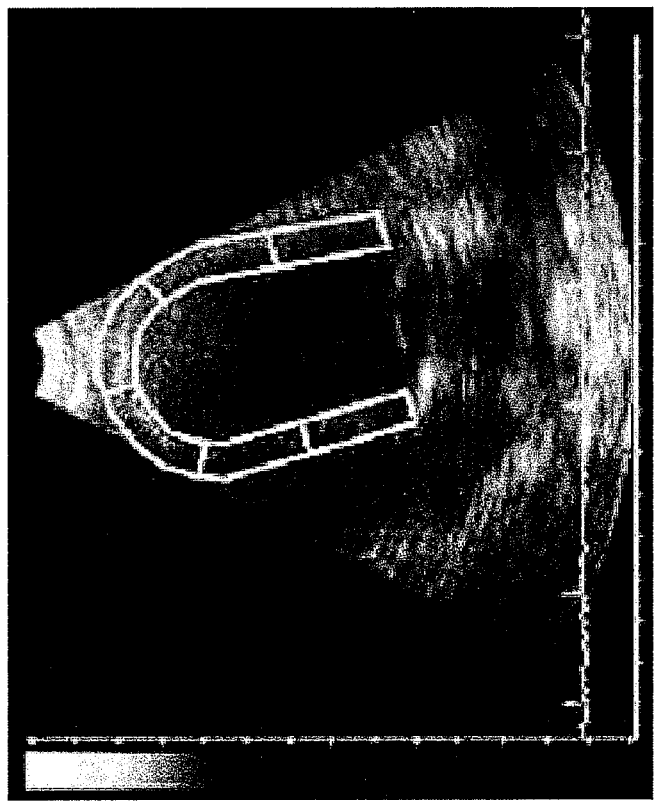
Figure 15A:
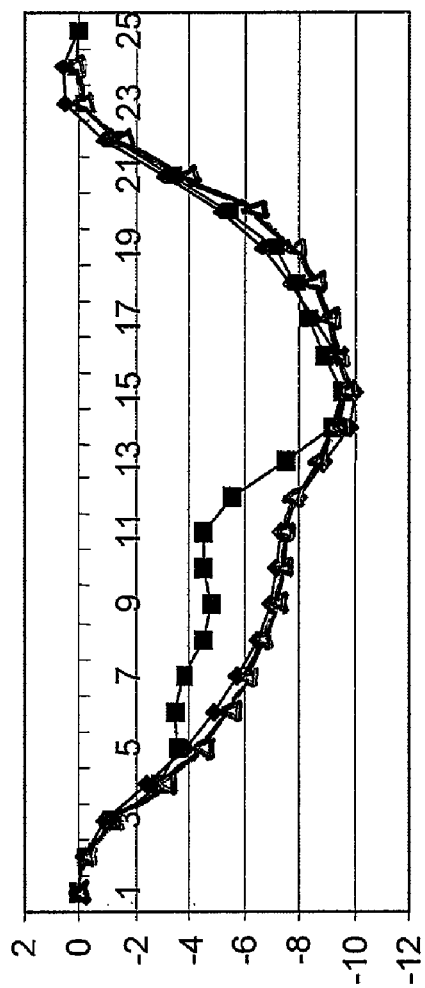
FIGS. 15a and 15b show the curves of strain vs time calculated tracking the second and sixth bottom-left reference point of FIG. 14a respectively. The two reference points have been taken on the same sequence of images by the same operator at different times (curves with squares and circles identifiers) and by a different operator (curve with triangles identifiers).
Figure 15B:
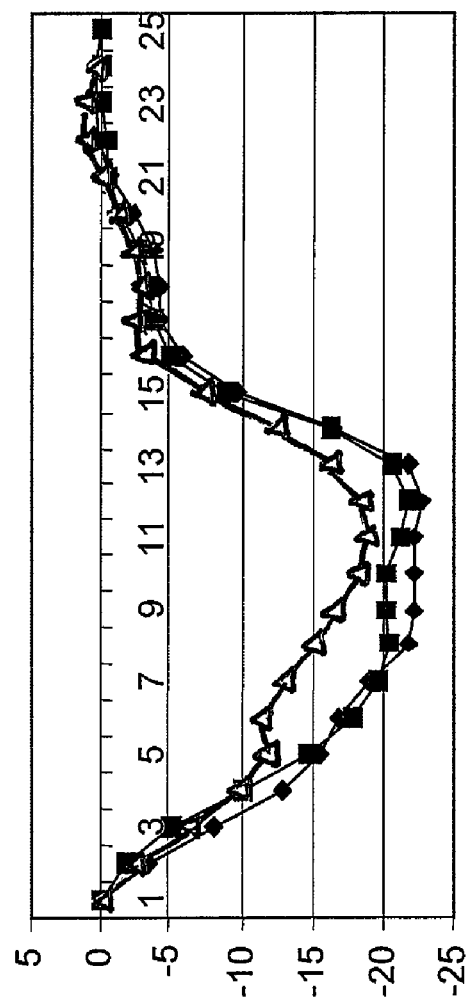

FIGS. 15*a* and 15*b* show the curves of strain vs time calculated on reference points 14 and 18 of FIG. 14*a* respectively, i.e. for the basal septum segment and the apical septum segment. The reference points have been taken on the same sequence of images by the same operator at different times (curves with squares and circles identifiers) and by a different operator (curve with triangles identifiers). As it can be seen, a certain degree of variability between curves still exists as expected. However this is reduced to an acceptable extent if compared to prior art where no control or standardization of reference points is provided.

Figure 16:
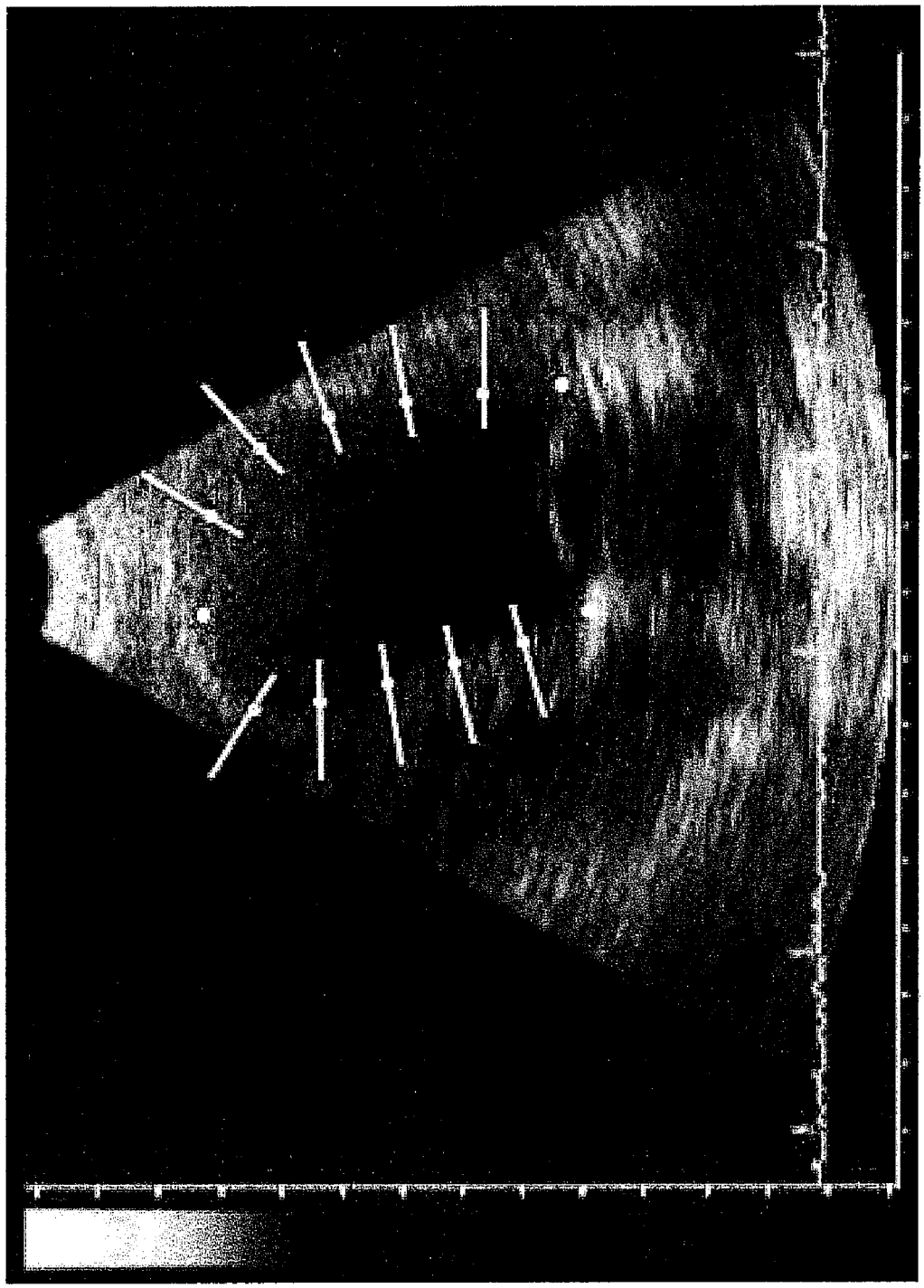
FIG. 16 shows an image with transmural cuts along an endocardial border.

The term superimposition used in the present description has to be interpreted broadly to both include a physical superimposition of two image layer and an automatic determination by software processing means. Also terms like resealing, aligning and the like have to be considered broadly to refer indistinctively either to rescaling/aligning the image frame with reference to the image reference and/or vice versa. In fact, although the method according to the invention has been mainly described with reference to a manual procedure performed, for example, by an operator who puts image rulers 1, 2 and 3 in the form of transparencies on the screen of an echographic apparatus or a monitor of a PC hosting echographic images previously taken and transferred for example via a DICOM interface, it can be appreciated by the skilled person that such method can also be performed by means of a computer software directly loadable in the memory of a computer which interact with an operator through standard input/output means. Such software could, for example, advantageously help the operator to position the reference points by providing grids or guiding tracks, like transmural cuts (as defined in EP-A-1522875), along the endocardial border as depicted in FIG. 16 or prompt the operator to input the number of regional segments to be used for dividing the endocardial border, all without departing from the guiding principle of the invention disclosed above and claimed below.

While the preferred embodiment of the invention has been illustrated and described in the drawings and foregoing description, the same is to be considered as illustrative and not restrictive in character, it being understood that all changes and modifications that come within the spirit of the invention are desired to be protected.

The invention claimed is:

1. A method for assessing motion, including deformation, of a moving structure from a sequence of at least two consecutive image frames of said structure, which images are timely separated by a certain time interval, the method comprising the following steps:
defining a certain number of reference points at least on one image frame of the sequence of image frames;
determining the velocity of motion of such reference points between two successive image frames;
characterised by:
rescaling the at least one image frame to fit within a reference window;
superimposing a reference image on such rescaled image frame; and
defining the reference points by matching points on the rescaled image frame to corresponding points on the reference image, wherein the corresponding points on the reference image belong to line or curve segments of the reference image, the reference points being defined by the intersection of such segments with a border line of the tissue or object automatically or manually drawn on the image frame.

2. The method according to claim 1, wherein the segments of the reference image are part of concentric lines regularly angularly spaced.

3. The method according to claim 2, wherein points are identified on the image frame, said points being used as landmarks to align the reference image on the image frame.

4. The method according to claim 3, wherein such landmarks are representative features of the structure which can be identified on such image frame.

5. The method according to claim 1, wherein the sequence of image frames is a sequence of consecutive B-mode, grey scale ultrasound images, the reference points being taken on a border line identified on at least one image of the sequence either manually or by means of an automatic border detection algorithm, said border being tracked to determine the new position of the reference points in at least one following image frame of the sequence so as to estimate the instant velocity of each reference point on the border line by dividing the displacement vector of each of the reference points from consecutive image frames by the time interval occurred between said consecutive image frames.

6. A method for assessing motion, including deformation, of a moving structure from a sequence of at least two consecutive image frames of said structure, which images are timely separated by a certain time interval, the method comprising the following steps:
defining a certain number of reference points at least on one image frame of the sequence of image frames;
determining the velocity of motion of such reference points between two successive image frames;
characterised by:
rescaling the at least one image frame to fit within a reference window;
superimposing a reference image on such rescaled image frame;
defining the reference points by matching points on the rescaled image frame to corresponding points on the reference image; and
wherein the reference points are positioned on a border line which is traced on an echographic image of the heart to identify the endocardial border.

7. The method according to claim 6, wherein the sequence of images frames represents the long axis view of the left ventricle, the landmarks being points identifying the cardiac apex and each of the two extremities of the annulus, the reference image being formed by a vertical line intersected by a number of divergent segments, preferably concentric, symmetrically disposed with reference to a median orthogonal segment.

8. The method according to claim 7, wherein the superimposition of the reference image on the at least one image frame comprises the steps of rototranslating the reference image to bring the upper segment to intercept the apex point, the lower segment to intercept one of the two annulus points and the median segment to be substantially orthogonal to the line passing through the apex and said one of the two annulus points.

9. The method according to claim 8, wherein the segments are seven, some or all the reference points on the at least one image frame being defined by the intersection of such segments with the endocardial border lying between the apex and said one of the two annulus points.

10. The method according to claim 6, wherein the reference points are thirteen, three of them being the reference points respectively taken on the apex and on both the extremities of the annulus, the remaining ten points being defined by alternatively choosing one of the two annulus points to determine five reference points on the septum endocardiac border and five reference points on the free wall endocardiac border.

11. The method according to claim 6, wherein the sequence of images frames represents the short axis basal or mid-cavity view, the landmark being a segment passing through the mitral valve or the papillar muscles, the reference image being formed by a bundle of concentric regularly angularly spaced lines, two lines of the bundle being orthogonal.

12. The method according to claim 11, wherein the superimposition of the reference image on the at least one image frame comprises the steps of rototranslating the reference image to bring one of the two orthogonal lines parallel to the landmark segment and the centre of the bundle in the middle of the ventricular cavity.

13. The method according to claim 12, wherein the orthogonal lines are provided with scales to guide the positioning of the centre of the bundle in the middle of the ventricular cavity.

14. The method according to claim 13, wherein the lines are six, the reference points on the at least one image frame being defined by the twelve intersections of such lines with the endocardial border.

15. The method according to claim 6, wherein the sequence of images frames represents the short axis apex view, the reference image being formed by a bundle of concentric regularly angularly spaced lines, two lines of the bundle being orthogonal, which reference image is superimposed on the at least one image frame with the centre of the bundle in the middle of the ventricular cavity.

16. The method according to claim 15, wherein the angular displacement of the reference image is determined by positioning one of the two orthogonal lines parallel to a landmark segment previously stored.

17. The method according to claim 16, wherein the lines are four, the reference points on the at least one image frame being defined by the eight intersections of such lines with the endocardial border.

18. The method according to claim 6, wherein the reference points on each image frame identify segments into which the left ventricle can be divided, each segment being identified by a series of three consecutive reference points, the median point of the series being taken as the representative point for assessing motion and/or deformation of each segment.

19. The method according to claim 18, wherein the segments into which the left ventricle can be divided in each echographic view are related and/or correspond to regional wall segments defined according to the recommendation of the American Society of Echocardiography.

20. The method according to claim 19, wherein motion and/or deformation is assessed by determining the velocity of motion and/or strain rate of such median reference points between consecutive image frames.

21. An apparatus for assessing motion, including deformation, of a moving structure from a sequence of at least two consecutive image frames of said structure, which images are timely separated by a certain time interval, the apparatus comprising input means for receiving the position of representative landmarks on at least one image of the sequence and processing means programmed for determining reference points representative of motion and/or deformation of the structure by scaling and/or superimposing said at least one image with a reference image, said landmarks being used for aligning said reference image onto said at least one image of the sequence, which reference points are determined by the intersection of a border line of the structure with line or curve segments forming said reference image.

22. The apparatus according to claim 21, wherein motion and/or deformation of the structure is evaluated by determining the velocity of motion of such reference points between two successive image frames by using Doppler methods and/or by tracking the movement of such reference points in consecutive image frames and dividing the displacement vector of each of the reference points from consecutive image frames by the time interval occurred between said consecutive image frames or by applying the so called particle image velocimetry technique abbreviated as PIV.

23. The apparatus according to claim 22, wherein deformation of the structure is evaluated by determining the spatial derivatives of velocities of the reference points which can be further integrated to obtain an estimation of strain.

24. The apparatus according to claim 21, wherein the processing means is programmed to carry out one or more of the method steps according to claim 1.

25. A generally transparent image ruler, comprising a series of diverging lines constructed and arranged to be manually positioned on a screen displaying at least an image frame of a sequence of image frames of a structure to determine reference points representative of motion and/or deformation of said structure by performing the method steps of claim 1.

26. The method according to claim 1, wherein points are identified on the image frame, said points being used as landmarks to align the reference image on the image frame.

27. The method according to claim 2, wherein segments are identified on the image frame, said segments being used as landmarks to align the reference image on the image frame.

28. A method for assessing motion, including deformation, of a moving structure from a sequence of at least two consecutive image frames of said structure, which images are timely separated by a certain time interval, the method comprising the following steps:
  defining a certain number of reference points at least on one image frame of the sequence of image frames;
  determining the velocity of motion of such reference points between two successive image frames;
  characterised by:
  rescaling the at least one image frame to fit within a reference window;
  superimposing a reference image on such rescaled image frame;

defining the reference points by matching points on the rescaled image frame to corresponding points on the reference image;

wherein the reference points are positioned on a border line which is traced on an echographic image of the heart to identify the endocardial border; and wherein the reference points are thirteen, three of them being the reference points respectively taken on the apex and on both the extremities of the annulus, the remaining ten points being defined by alternatively choosing one of the two annulus points to determine five reference points on the septum endocardiac border and five reference points on the free wall endocardiac border.

29. A method for assessing motion, including deformation, of a moving structure from a sequence of at least two consecutive image frames of said structure, which images are timely separated by a certain time interval, the method comprising the following steps:

defining a certain number of reference points at least on one image frame of the sequence of image frames;

determining the velocity of motion of such reference points between two successive image frames;

characterised by:

rescaling the at least one image frame to fit within a reference window;

superimposing a reference image on such rescaled image frame;

defining the reference points by matching points on the rescaled image frame to corresponding points on the reference image;

wherein the reference points are positioned on a border line which is traced on an echographic image of the heart to identify the endocardial border;

wherein the sequence of images frames represents the short axis basal or mid-cavity view, the landmark being a segment passing through the mitral valve or the papillar muscles, the reference image being formed by a bundle of concentric regularly angularly spaced lines, two lines of the bundle being orthogonal;

wherein the superimposition of the reference image on the at least one image frame comprises the steps of rototranslating the reference image to bring one of the two orthogonal lines parallel to the landmark segment and the center of the bundle in the middle of the ventricular cavity;

wherein the orthogonal lines are provided with scales to guide the positioning of the center of the bundle in the middle of the ventricular cavity; and wherein the lines are six, the reference points on the at least one image frame being defined by the twelve intersections of such lines with the endocardial border.

* * * * *